United States Patent [19]

Fogassy et al.

[11] Patent Number: 4,508,919
[45] Date of Patent: Apr. 2, 1985

[54] PROCESS FOR THE PREPARATION OF OPTICALLY ACTIVE CYCLOPROPANE CARBOXYLIC ACIDS

[75] Inventors: Elemér Fogassy; László Toke; Ferenc Faigl; Rudolf Sóós; József Bozzay; Rezso Kolta; József Nemes; Péter Bencsik, all of Budapest, Hungary

[73] Assignee: Chinoin Gyogyszer es Vegyeszeti Termekek Gyara Rt., Budapest, Hungary

[21] Appl. No.: 555,187

[22] Filed: Nov. 25, 1983

[30] Foreign Application Priority Data

Nov. 25, 1982 [HU] Hungary ............................. 3789/82

[51] Int. Cl.³ ............................................. C07B 19/00
[52] U.S. Cl. ..................................... 562/401; 562/506
[58] Field of Search ................................ 562/401, 506

[56] References Cited

U.S. PATENT DOCUMENTS 4,196,304 4/1980 Naumann ............................. 562/401
4,229,593 10/1980 Kondo et al. ....................... 562/401
4,328,173 5/1982 Jolly et al. .......................... 562/401

Primary Examiner—Natalie Trousof
Assistant Examiner—Vera C. Clarke
Attorney, Agent, or Firm—Karl F. Ross; Herbert Dubno

[57] ABSTRACT

The invention relates to a process for the preparation of enantiomers of trans vinyl-cyclopropane carboxylic acids of the formula I,

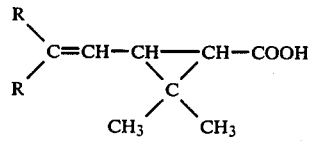

wherein R is a methyl group or chlorine atom, by resolution of racemic trans compound or mixture of racemic cis and trans compounds by using (+)- or (−)-N-(1-formamido-2,2,2-trichloroethyl)-piperazine as a resolving agent in a polar solvent then separating the crystallizing salt of (+)-trans carboxylic acid and (−)-resolving agent or (−)-trans carboxylic acid and (+)-resolving agent from the mother liquor by filtration and obtaining the enantiomers by acidifying the mother liquor or the salts suspended in water followed by extraction with a solvent and evaporation.

The products so obtained may be used as starting materials for the preparation of insecticides.

9 Claims, No Drawings

PROCESS FOR THE PREPARATION OF OPTICALLY ACTIVE CYCLOPROPANE CARBOXYLIC ACIDS

The invention relates to a process for the preparation of enantiomers of trans-vinyl-cyclopropane carboxylic acids of the formula (I),

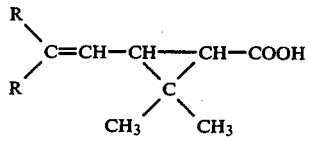

wherein R is methyl group or chlorine atom, by resolution of the racemic trans compound or of a mixture of racemic cis and trans isomers with (+)- or (−)-N-)1-formamido-2,2,2-trichloroethyl)-piperazine as a resolving agent in a polar solvent then separating the salt of the (+)-trans carboxylic acid and the (−)-resolving agent or that of the (−)-trans carboxylic acid and the (+)-resolving agent being crystallized from the mother liquor by filtration then obtaining the enantiomers by acidifying the mother liquor and the salts suspended in water followed by extraction with a solvent and evaporation.

R represents, whereever it occurs, groups as stated above, and therefore its definitions will not be repeated.

According to a preferred embodiment of the invention an aqueous medium is used as a solvent and the resolution is carried out in alkaline pH interval, preferably at pH values of 8.0 to 8.5 and optionally the aqueous solution of the racemate is processed with a base and that of the resolving agent with an acid and the solutions obtained are combined. The resolving agent is used suitably in an amount equivalent to or less than the amount of the corresponding trans enantiomer.

For the preparation of the derivatives of the enantiomers of the acids of formula (I), which derivatives have different biological activity, separation and preparation, respectively, of the possible isomers are required. The derivatives are prepared by the use of enantiomers obtained in the course of resolution of the different 1,3-cis and -trans isomers. Mixtures of cis and trans isomers of the racemic carboxylic acids are formed in the course of different syntheses. The amount of the trans isomers generally exceeds that of the cis isomers. Processes, which start from racemic trans carboxylic acids, are also known for the preparation of the enantiomers, however, separation of racemic cis and trans carboxylic acids is required first. According to the British patent specification No. 1,220,160 (±)-2,2-dimethyl-3-isobutenyl-1,3-trans-cyclopropane-1-carboxylic acid is resolved in methanol with D(−)-threo-1-p-nitrophenyl-2-dimethyl-aminopropane-1,3-diol and the crystalline diastereomeric salt obtained, which contains (+)-carboxylic acid, is suspended in isopropyl ether, dried then crystallized from a mixture of isopropyl ehter and petroleum ether. According to the British patent specification No. 1,300,840 the resolution of the carboxylic acid is carried out with L-lysine also in methanol and the diastereomer containing the (+)-carboxylic acid crystallizes from the reaction mixture in this case as well. According to the U.S. Pat. No. 3,842,125 racemic trans carboxylic acid is resolved in ethanol solution with (−)-alpha-(1-naphthyl)-ethylamine then the diastereomeric salt containing (+)-carboxylic acid is recrystallized from ethanol.

According to the British patent specification No. 1,178,423 racemic trans carboxylic acid is used with quinine as resolving agent in ethanol solution. The diastereomeric salt containing the (−)-carboxylic acid crystallizes from the solution and the (+)-carboxylic acid is obtained from the mother liquor after recrystallization from ethanol. According to the British patent specification No. 1,369,730 mixtures of racemic cis and trans carboxylic acids can also be used as starting material. The resolution is carried out with (+)-alpha-phenyl-beta-p-tolyl-ethylamine in 85% aqueous methanol and the crystalline salt obtained contains the mixture of (+)-cis and (+)-trans carboxylic acids.

Based on these known processes pure enantiomers can only be prepared if cis and trans isomers are separated first. Preparation of optically pure enantiomers can be accomplished, if possible at all, only by recrystallization. Yields for the enantiomers were 50 to 70%. The price of the resolving agent is high. The costs of the processes and further increased by the prices of the solvents used. Further disadvantage of the above processes is that only one of the antipodes is obtained and there is no reference for the use of the other antipode.

The present invention is based on the discovery that (+)- or (−)-N-(1-formamido-2,2,2-trichloroethyl)-piperazine is a suitable resolving agent for the preparation of trans-(+)- or (−)-carboxylic acids starting from the racemic trans-2,2-dimethyl-3-disubstituted-vinyl-cyclopropane-carboxylic acids and from the mixture of cis and trans isomers of these racemic carboxylic acids, respectively.

This resolving agent can be synthesized according to the German Offenlegungsschrift No. 2,351,707. This compound has not been applied as a resolving agent heretofore. It can be used for the resolution of cyclopropane-carboxylic acids in different solvents fairly well, especially in water.

During the resolution of a racemic mixture of carboxylic acids with the (+)-resolving agent always the (−)-1S,3S-, and with (−)-resolving agent always the (+)-1R,3R-carboxylic acid precipitate as a salt, i.e. (+)-resolving agent forms a poorly soluble and well crystallizable diastereomeric salt with the (−)-trans-carboxylic acid, while the (−)-resolving agent forms the salt with (+)-trans-carboxylic acid.

It is not necessary to use the resolving agent in an amount equivalent to that of the racemate. Preferably, its amount should be equivalent to or less than that of the trans enantiomer of the racemic mixture of the cis and trans isomers. If non-aqueous solution is used only the racemate and the resolving agent are put into the mixture.

In aqueous solution the resolution is carried out at alkaline pH, preferably at pH values of 8.0–8.5. The resolution can also be carried out in such way that the aqueous solution of the racemate is prepared with an alkali and that of the resolving agent with an acid and the solutions obtained are combined. Adjustment of pH value is performed with alkali if required, preferably with ammonia.

The crystalline diastereomeric salts precipitated from the reaction mixture are separated by filtration. From the salts obtained the optically active acids are set free in aqueous solution or suspension using mineral acids thereafter extracted with an organic solvent immiscible with water. The enantiomers are obtained from the extracts after drying and evaporating the solvent.

The organic mother liquor obtained after filtration of the diastereomeric salts is evaporated; the residue water is added, whereafter the aqueous mother liquors are directly reacted with mineral acids and the enantiomers are separated by extraction as described above.

If further purification is required, the enantiomers obtained are resolved with the corresponding resolving agent according to the above processes. However, it is more advantageous if the enantiomers without the optical purity required are crystallized per se, preferably with cooling. In this case the contaminating racemic cis- and trans-carboxylic acids, respectively, crystallize and these can be separated by filtration. The mother liquor contains the melt of the (+)- or (−)-trans enantiomer having the optical purity required.

The purification of the enantiomers can also be carried out by recrystallization of the diastereomeric salts obtained from solvents or by selective setting free of the enantiomers from the aqueous solution or suspension of the salts by addition of an alkali or an acid in the calculated amount. In this latter case the insoluble diastereomeric salt is filtered off and the enantiomer is obtained from this salt according to the processes described above.

From fractions obtained by the purification processes stated above, which contain the racemic trans carboxylic acid, the (+)- or (−)-trans enantiomers can also be separated by repeated resolution. By the use of these processes approximately 90% of (+)- or (−)-trans enantiomer content of the starting racemates can be obtained with an optical purity of 90% or more.

The resolving agent used in the above processes remains in the aqueous mother liquor from which it crystallizes on alkalizing of the solution and, in this way, it may be used again for resolution. It is also possible to use for resolution in aqueous medium the aqueous mother liquor containing the resolving agent.

The resolving agent can also be obtained from the aqueous mother liquor by precipitating it in form of a poorly soluble salt with an acid, such as hydrochloric acid.

The resolving agent used can be obtained by the above processes in a yield above 80% and in a quality suitable for use in further resolutions.

The process according to the invention is shown, without limiting its scope, by way of the following Examples.

EXAMPLE 1

3.36 g (0.022 mole) of racemic 2,2-dimethyl-3-isobutenyl-cyclopropane carboxylic acid (cis/trans=0/100) are suspended in 10 ml of water then the pH is adjusted with 10% sodium hydroxide solution to 7.0. The solution obtained is heated to 40° C. and an aqueous solution of 1.5 g (0.006 mole) of (−)-N-(1-formamido-2,2,2-trichloroethyl)-piperazine being (adjusted with 10% hydrochloric acid solution to pH 7) are added. For a short time the mixture remains solution, the pH value of which is adjusted with concentrated ammonia solution to 8. The crystals precipitated are filtered and washed with water. The salt obtained (2.9 g) is suspended in water and acidified to pH 1 with concentrated hydrochloric acid. An oily precipitate is formed which is extracted twice each 20 ml of chloroform each time and then the combined chloroform solution is dried and evaporated. Thus 0.9 g of (+)-2,2-dimethyl-3-isobutenyl-cyclopropane carboxylic acid are obtained as an oily product, yield 53.6%, $[\alpha]_D^{20} = +24°$ (c:2, chloroform). A further 2.5 g of product can be obtained from the mother liquor, $[\alpha]_D^{20} = -5°$ (c:2, chloroform).

EXAMPLE 2

2.1 g (0.01 mole) of racemic 2,2-dimethyl-3-(dichlorovinyl)-cyclopropane carboxylic acid (cis/trans=46/54) are dissolved in 15 ml of water and the pH value is adjusted with 10% sodium hydroxide solution to 7. The solution is heated to 40° C. then 1.05 g of (−)-N-(1-formamido-2,2,2-trichloro-ethyl)-piperazine dissolved in 5 ml of water by adjusting the pH value to 7 with hydrochloric acid are added. The precipitated diastereomeric salt is filtered off and washed with water. The salt obtained (2.5 g) is suspended in 10 ml of water, the pH value is adjusted with concentrated hydrochloric acid to 1 and this mixture is extracted with 2×10 ml of chloroform. The combined chloroform solution is dried and evaporated. 0.8 g of an oily residue, the (+)-2,2-dimethyl-3-(dichlorovinyl)-cyclopropane carboxylic acid are obtained. Yield 85.7%, cis/trans=60/40, $[\alpha]_D^{20} = +27.5°$ (c:2, chloroform). 1.3 g of (−)-2,2-dimethyl-3-(dichloro-vinyl)-cyclopropane carboxylic acid are obtained from the mother liquor according to the former process. cis/trans=40/60, $[\alpha]_D^{20} = -10°$ (c:2, chloroform).

EXAMPLE 3

3.3 g (0.02 moles) of 2,2-dimethyl-3-isobutenyl-cyclopropane carboxylic acid (cis)trans=10/90) are dissolved in 5 ml of methanol and 1.6 g (0.006 moles) of (−)-N-(1-formamido-2,2,2-trichloroethyl)-piperazine dissolved in 10 ml of methanol are added with stirring. The mixture is cooled to −2° C., the crystals precipitated are filtered off (2.4 g). The filtrate is evaporated in vacuo, the residue is dissolved in 10 ml of water and the pH is adjusted with 20% hydrochloric acid solution to 1. The oily precipitate obtained is extracted with 15 ml of chloroform the chloroform phase is then dried and evaporated. So 2.6 g product are obtained. $[\alpha]_D^{20} = -4°$ (c:2, chloroform).

10 ml of water are added to the above 2.4 g salt and the pH value of this suspension is adjusted 20% with hydrochloric acid solution to 1. The solution obtained is extracted with chloroform, the chloroform solution is then dried and evaporated. 0.5 g of 2,2-dimethyl-3-isobutenyl-cyclopropane carboxylic acid are obtained. $[\alpha]_D^{20} = +23°$ (c:5, chloroform).

EXAMPLE 4

A solution of 3.36 g of racemic 2,2-dimethyl-3-isobutenyl-cyclopropane carboxylic acid (cis/trans=10/90) in 5 ml of anhydrous ethanol is mixed at 25° C. with a suspension of 1.6 g of (−)-N-(1-formamido-2,2,2-trichloro-ethyl)-piperazine in 10 ml of anhydrous ethanol. The clear solution obtained is cooled to −2° C. then the precipitate is filtered in cold (0.9 g).

The filtrate is evaporated in vacuo, the residue is dissolved in 10 ml of water, the pH value is adjusted with 20% hydrochloric acid solution to 1. The oily precipitate formed is extracted with chloroform, the chloroform solution is then dried and evaporated. 2.6 g product are obtained. $[\alpha]_D^{20} = -4°$ (c:5, chloroform).

The 0.9 g diastereomeric salt is processed in the same way as the residue of the filtrate. After evaporating the chloroform phase 0.35 g product are obtained. $[\alpha]_D^{20} = +26°$ (c:3.5, chloroform).

EXAMPLE 5

To a solution of 3.36 g of racemic 2,2-dimethyl-3-isobutenyl-cyclopropane carboxylic acid (cis/trans=10/90) in 15 ml acetone 1.6 g (−)-N-(1-formamido-2,2,2-trichloro-ethyl)-piperazine are added under stirring. The reaction mixture is further stirred under cooling and the salt precipitated is washed with cold acetone. So 2.6 g product are obtained. The filtrate is evaporated in vacuo and the residue is further processes according to Example 3. So 2.1 g product are obtained, $[\alpha]_D^{20} = -5°$ (c:5, chloroform). The 2.6 g of diastereomeric salt is processed also according to Example 3. So 0.8 g product are obtained $[\alpha]_D^{20} = +22.5°$ (c:3.85, chloroform).

EXAMPLE 6

4.5 g of isomeric mixture containing (+)-2,2-dimethyl-3-isobutenyl-cyclopropane carboxylic acid $[\alpha]_D^{20} = +15.5°$ (c:2, chloroform) are dissolved in 20 ml of water with 10% sodium hydroxide solution at pH 7. The solution is heated to 40° C. and the solution of 3.5 g of (−)-N-(1-formamido-2,2,2-trichloroethyl)-piperazine in 10 ml of water, neutralized to pH 7 with hydrochloric acid, is added. The mixture is filtered and the salt is washed with water. 10 ml of water are added to this diastereomeric salt (7.5 g), the pH of the solution is acidified to 1 with concentrated hydrochloric acid and the further processing is carried out according to Example 3. 2.3 g of (+)-2,2-dimethyl-3-isobutenyl-cyclopropane carboxylic acid are obtained, $[\alpha]_D^{20} = +26°$ (c:2, chloroform). From the mother liquor 2.1 g product are obtained with an $[\alpha]_D^{20}$ value of −1.0° (c:2, chloroform).

EXAMPLE 7

2.02 g of (+)-2,2-dimethyl-3-isobutenyl-cyclopropane carboxylic acid (cis/trans=30/70) are dissolved in 5 ml of water containing 0.48 g of sodium hydroxide. 0.94 g of (+)-N-(1-formamido-2,2,2-trichloroethyl)-piperazine are also dissolved in 5 ml of water by adjusting the pH with concentrated hydrochloric acid to 6 to 7. The solutions are combined and after standing the diastereomeric salt is filtered off. 1.6 g salt are obtained. The diastereomeric salt is decomposed according to Example 1. So 0.6 g product are obtained (83.2% calculated on the trans isomer), $[\alpha]_D^{20} = -20°$ (c:4, chloroform). To the mother liquor of the 1.6 g salt 0.9 g of (−)-N-(1-formamido-2,2,2-trichloroethyl)-piperazine hydrochloride are added and crystalline material is precipitated. The other diastereomeric salt is filtered off after 2 hours standing, its weight is 1.5 g. The decomposition of the salt is carried out as described in Example 1. 0.5 g product are obtained $[\alpha]_D^{20} = +25.6°$ (c:3, chloroform). The filtrate is processed according to Example 1, weight of the evaporation residue is 0.5 g, $[\alpha]_D^{20} = 0°$ (c:5, chloroform).

EXAMPLE 8

2.3 g of isomeric mixture containing (−)-2,2-dimethyl-3-isobutenyl-cyclopropane carboxylic acid $[\alpha]_D^{20} = -5°$ (c:2, chloroform) are left to stand at room temperature for 24 hours. Weight of the crystalline precipitate formed is 1.2 g, $[\alpha]_D^{20} = 1.5°$ (c:2, chloroform), weight of residual oil is 1.0 g $[\alpha]_D^{20} = -11.0°$ (c:2, chloroform).

EXAMPLE 9

2.9 g of oily isomeric mixture $[\alpha]_D^{20} = +7°$ (c:2, chloroform) containing (+)-2,2-dimethyl-3-isobutenyl-cyclopropane carboxylic acid are left to stand at room temperature for 24 hours. 1.6 g of crystalline product are obtained, $[\alpha]_D^{20} = +19.0°$ (c:2, chloroform).

EXAMPLE 10

6.5 g of regenerated 2,2-dimethyl-3-isobutenyl-cyclopropane carboxylic acid (cis/trans=0/100, $[\alpha]_D^{20} = +4°$ (c:2, chloroform) and 2.52 g of (−)-1-(formamido-2,2,2-trichloroethyl)-piperazine are reacted as described in Example 1. Weight of the (+)-enantiomer obtained from the diastereomeric salt is 1.3 g (35%), $[\alpha]_D^{20} = +25°$ (c:1, chloroform). 4.5 g product can be separated from the mother lye $[\alpha]_D^{20} = -6°$ (c:1, chloroform).

EXAMPLE 11

3.0 g of diastereomeric salt (from which (+)-trans-2,2-dimethyl-3-isobutenyl cyclopropane carboxylic acid with a specific rotation of +14° may be obtained) are dissolved in 18 ml of hot methyl ethyl ketone. The solution is filtered hot then cooled gradually to 0° C. The crystals precipitated are filtered off, their weight is 2.4 g (80%). The salt is processed as described in Example 1, the weight of the enantiomer obtained is 0.77 g, $[\alpha]_D^{20} = +21°$ (c:4.5, chloroform). The filtrate is evaporated, the residue is dissolved in water, the solution is acidified to pH 1, the oily phase is extracted with chloroform. The chloroform solution is evaporated after drying, so 0.3 g residue are obtained $[\alpha]_D^{20} = -6.6°$ (c:1.5, chloroform).

EXAMPLE 12

1.4 g of (+)-2,2-dimethyl-3-isobutenyl-cyclopropane carboxylic acid-(−)-N-(1-formamido-2,2,2-trichloroethyl)-piperazine salt are suspended in 10 ml of water then the pH is adjusted with 20% hydrochloric acid to 1 and the oil formed is extracted with chloroform. The remaining acidic solution is alkalized to pH 11 under cooling with 10 molar sodium hydroxide solution. The (−)-N-(1-formamido-2,2,2-trichloroethyl)-piperazine base slowly crystallizes, its weight is 0.6 g (70%), $[\alpha]_D^{20} = -60°$ (c:0.8, methanol).

EXAMPLE 13

2.4 g of (+)-2,2-dimethyl-3-isobutenyl-cyclopropane carboxylic acid-(−)-N-(1-formamido-2,2,2-trichloroethyl)-piperazine salt are suspended in 15 ml of chloroform then 1 ml of water and 1 ml of 37% hydrochloric acid are added. The mixture is cooled below 10° C. under stirring then the (−)-N-(1-formamido-2,2,2-trichloroethyl)-piperazine hydrochloride is filtered off, its weight is 1.2 g (70%). The specific rotation of the base setted free from the salt is $[\alpha]_D^{20} = -59°$ (c:1, methanol).

EXAMPLE 14

The aqueous solution obtained according to the process described in Example 12 is evaporated till the concentration of the (−)-N-(1-formamido-2,2,2-trichloroethyl)-piperazine becomes 1.6 g/10 ml then the pH value of the solution is adjusted with 10 molar sodium hydroxide to 6 to 7 thereafter used for further resolution according to Example 1.

We claim:

1. Process for the preparation of enantiomers of trans vinyl-cyclopropane carboxylic acids of the formula I

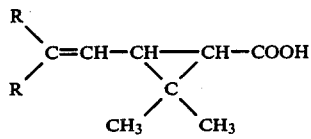

wherein R is methyl or chlorine, by resolution of racemic trans compound or mixture of racemic trans and cis compounds, wherein an effective amount of (+)- or (−)-N-(1-formamido-2,2,2-trichloro.ethyl)-piperazine is used as a resolving agent in a polar solvent, then the crystallizing salt of (+)-trans carboxylic acid and (−)-resolving agent or (−)-trans carboxylic acid and (+)-resolving agent is separated from the mother liquor by filtration then the enantiomers are obtained by acidifying the mother liquor or the salts suspended in water followed by extraction with a solvent and evaporation.

2. A process according to claim 1, wherein as solvent an aqueous medium is used and the resolution is carried out in an alkaline pH and the aqueous solution of the racemate is processed optionally with an alkali and that of the resolving agent with an acid and these solution are combined.

3. A process according to claim 1, wherein the resolving agent is used in an amount equivalent to or less than the amount of the corresponding trans enantiomer.

4. A process according to claim 1, wherein the enantiomers obtained are purified with repeated resolution and optionally, the enantiomers of the resolving agent are used alternately.

5. A process according to claim 1, wherein the enantiomers without the optical purity required are purified by crystallization in such manner that precipitated crystalline racemic cis or racemic trans carboxylic acid is separated by filtration from the melt of the (+)- and (−)-trans enantiomer, respectively.

6. A process according to claim 1, wherein the diastereomeric salts without the optical purity required are purified by recrystallization from a solvent or by fractionated setting free and extraction.

7. A process according to claim 1, wherein the fraction obtained while purifying the enantiomers containing the racemic trans carboxylic acid is repeatedly resolved.

8. A process according to claim 1, wherein the resolving agent is regenerated for further use in such a way that the aqueous mother liquor containing the resolving agent is used as a solvent for further resolution or the resolving agent is precipitated with an alkali from the aqueous mother liquor or is crystallized from water as a salt with an achiralic acid.

9. The process defined in claim 1 wherein the polar solvent is selected from the group consisting of water, methanol, ethanol, acetone and methylethyl ketone.

* * * * *